United States Patent [19]

Finney

[11] Patent Number: 4,682,589
[45] Date of Patent: Jul. 28, 1987

[54] PENILE PROSTHESIS

[75] Inventor: Roy P. Finney, Bayport, Fla.

[73] Assignee: Medical Engineering Corporation, Racine, Wis.

[21] Appl. No.: 810,420

[22] Filed: Dec. 18, 1985

Related U.S. Application Data

[60] Continuation-in-part of Ser. No. 459,776, Jan. 21, 1983, which is a division of Ser. No. 313,729, Oct. 22, 1981, Pat. No. 4,378,792, which is a division of Ser. No. 150,231, May 15, 1980, Pat. No. 4,318,396, and Ser. No. 680,746, Dec. 12, 1984, Pat. No. 4,622,958.

[51] Int. Cl.$^4$ .............................................. A61F 2/26
[52] U.S. Cl. ..................................................... 128/79
[58] Field of Search .......................................... 128/79

[56] References Cited

U.S. PATENT DOCUMENTS

| | | |
|---|---|---|
| 3,853,122 | 12/1974 | Strauch et al. . |
| 3,954,102 | 5/1976 | Buuck . |
| 4,009,711 | 3/1977 | Uson . |
| 4,201,202 | 5/1980 | Finney et al. . |
| 4,267,829 | 5/1981 | Burton et al. . |
| 4,318,396 | 3/1982 | Finney . |
| 4,342,308 | 8/1982 | Trick .......................... 128/79 |
| 4,353,360 | 10/1982 | Finney et al. . |
| 4,360,010 | 11/1982 | Finney . |
| 4,364,379 | 12/1982 | Finney . |
| 4,383,525 | 5/1983 | Scott et al. . |
| 4,399,811 | 8/1983 | Finney et al. ............... 128/79 |
| 4,399,812 | 8/1983 | Whitehead .................. 128/79 |
| 4,550,720 | 11/1985 | Trick .......................... 128/79 |
| 4,572,168 | 2/1986 | Fischell ...................... 128/79 |
| 4,594,997 | 6/1986 | Hakky ........................ 128/79 |
| 4,596,242 | 6/1986 | Fischell ...................... 128/79 |

OTHER PUBLICATIONS

Hakky, PCT Application WO 80/00302.

Primary Examiner—Robert Peshock
Assistant Examiner—Cary E. Stone
Attorney, Agent, or Firm—Quarles & Brady

[57] ABSTRACT

An inflatable penile implant includes a pressure chamber, a reservoir for pressurizing fluid and an expandable member in the reservoir for transferring fluid under pressure to the pressure chamber to make it rigid.

2 Claims, 11 Drawing Figures

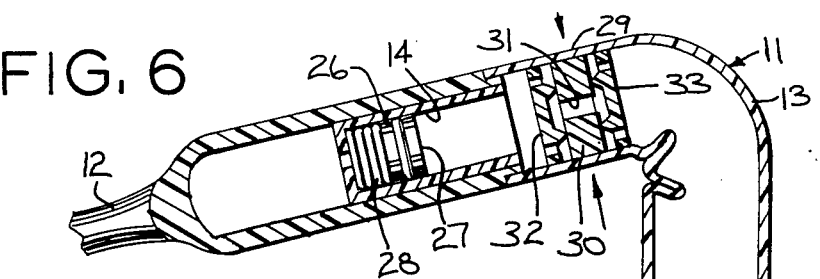
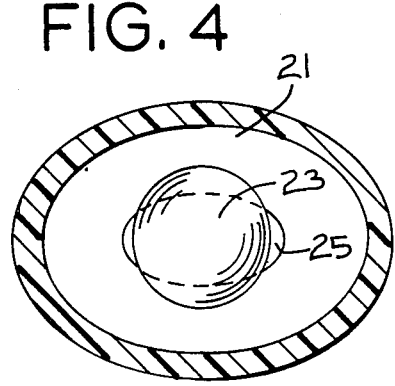
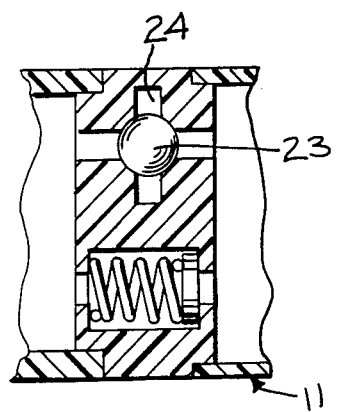
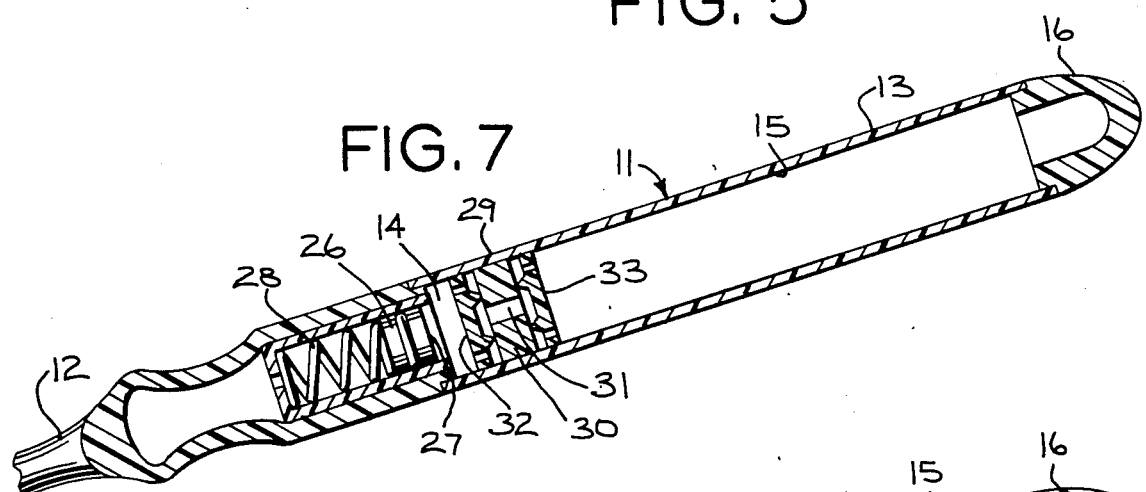
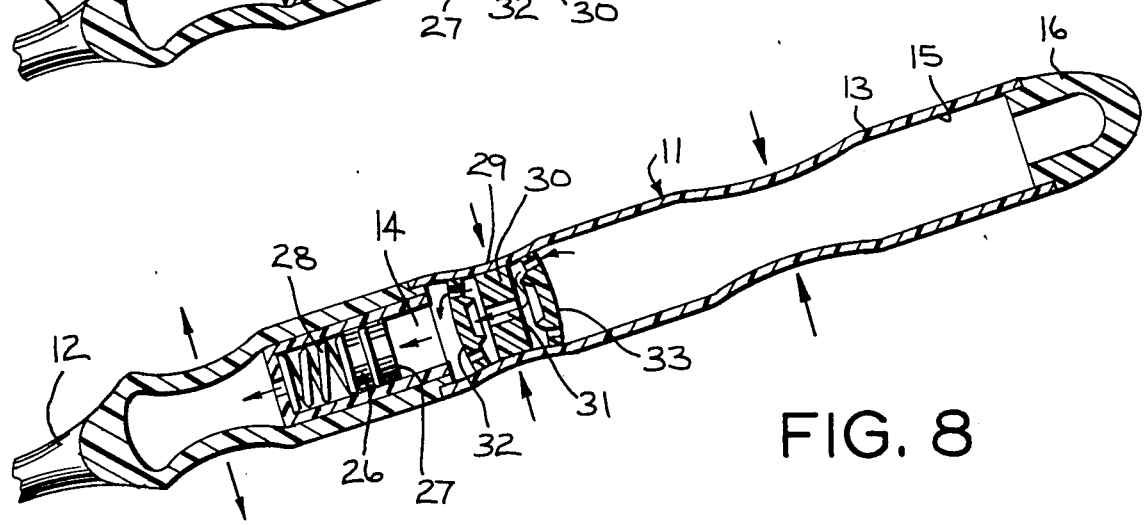

PENILE PROSTHESIS

RELATED CASES

This is a continuation-in-part of my application Ser. No. 459,776 filed Jan. 21, 1983, which is a division of application Ser. No. 313,729, filed Oct. 22, 1981, now U.S. Pat. No. 4,378,492, which is a division of application Ser. No. 150,231, filed May 15, 1980, now U.S. Pat. No. 4,318,396 and my application Ser. No. 680,746 filed Dec. 12, 1984, now U.S. Pat. No. 4,622,958.

FIELD OF THE INVENTION

The present invention relates to a penile prosthesis. More particularly, it relates to an inflatable penile prosthesis which is adapted to be implanted in man for treatment of erectile impotence.

BACKGROUND OF THE INVENTION

There are instances of erectile impotence in which the patient does not respond to more conventional therapy and the surgical implanting of a penile prosthesis may be the only practical means of remedying the impotency.

Several types of penile prostheses have been employed in the past. One type of penile prosthesis is a pair of rods of suitable stiffness which are surgically implanted into the corpus cavernosum of the penis. One disadvantage of some of the rod-type implants is the permanent stiffness of the rod which can be a source of physical pain and/or embarrassment to the patient. The prostheses disclosed in U.S. Pat. Nos. 3,893,476 and 4,066,037 are representatives of the rod type prostheses.

Another type of penile prosthesis which is available is the inflatable prosthesis of U.S. Pat. No. 3,954,102. The patented prosthesis includes two fairly long inflatable and distensible tubes that are surgically implanted in the corpus cavernosum of the penis. Each of the two tubes is connected by tubing to a pressure bulb of inflating fluid which is implanted elsewhere in the body. Because of the volume required to inflate, distend, pressurize and rigidize the inflatable tubes, the pressure bulbs are relatively large.

Recently penile implants have been patented which are essentially cylinders which contain a hydraulic system comprising a pressure chamber, a reservoir and a pump for transferring fluid from the reservoir to the pressure chamber. The pump must be manually squeezed to transfer the fluid to the pressure chamber. Representative of such implants are those of U.S. Pat. Nos. 4,353,360, 4,267,829 and 4,383,525.

Although the previously patented prostheses are useful and valuable devices, there is a need for an improved penile prosthesis which is easier to operate and which does not require pumping for an erection.

SUMMARY OF THE INVENTION

It is the general object of the present invention to disclose an improved penile prosthesis.

The penile prosthesis of the present invention comprises a pair of penile implants. Each of the implants is an elongated cylindrical member which is adapted to be implanted into the corpus cavernosum. The cylinder includes a proximal portion for implanting in the root end of the corpus and an elongated flexible, hollow distal portion having a non-distensible pressure chamber and a conical tip which is adapted to be implanted in the corpus cavernosum of the pendulus penis. The cylinder also includes an internal reservoir for fluid to fill and pressurize the pressure chamber to make the non-distensible distal portion rigid and to stiffen the penis and means for automatically transferring fluid from the reservoir to the pressure chamber without pumping.

In one embodiment, the means for transferring fluid to the pressure chamber is a gas filled bladder which is maintained in a compressed or non-expanded state in the reservoir by the fluid pressure in the reservoir which is higher than the fluid pressure in the pressure chamber.

In a second embodiment, the means for transferring fluid is a spring driven piston located in the reservoir. The spring is normally compressed by the fluid pressure in the reservoir which is higher than that in the pressure chamber. When a valve is opened to relieve the pressure in the reservoir the spring is released and it expands to cause the piston to transfer fluid from the reservoir under pressure into the pressure chamber.

In another embodiment of the piston type, the spring is normally held compressed by a ball point pen type latch-unlatch mechanism which is both latched and released by moving the piston back.

The proximal portion of implant of the present invention is preferably an anchoring stem which is relatively stiff so that it can be implanted into the root end of the corpus cavernosum to support the implant. The remainder of the implant is of a less stiff and softer material which reduces the risk of tissue irritation. When not pressurized the cylinder is flexible and permits the pendulus penis to assume a normal flaccid position. The tip at the distal end of the implant is soft and paraboloidal to fit the end of the corpus cavernosum, and to enhance the physiological compatibility of the implant.

BRIEF DESCRIPTION OF THE DRAWINGS

In the drawings:

FIG. 4 is an enlarged sectional view taken along line 4—4 in FIG. 3;

FIG. 5 is a view, in section, of an alternative valve system;

FIG. 6 is a side view, partly in section, of a penile implant of the present invention with a spring driven piston in the reservoir;

FIG. 7 is a side view similar to FIG. 5 except that the implant is pressurized;

FIG. 8 is a side view similar to FIG. 6 showing the pressure chamber being depressurized.

BEST MODE OF CARRYING OUT THE INVENTION

Figure 1:
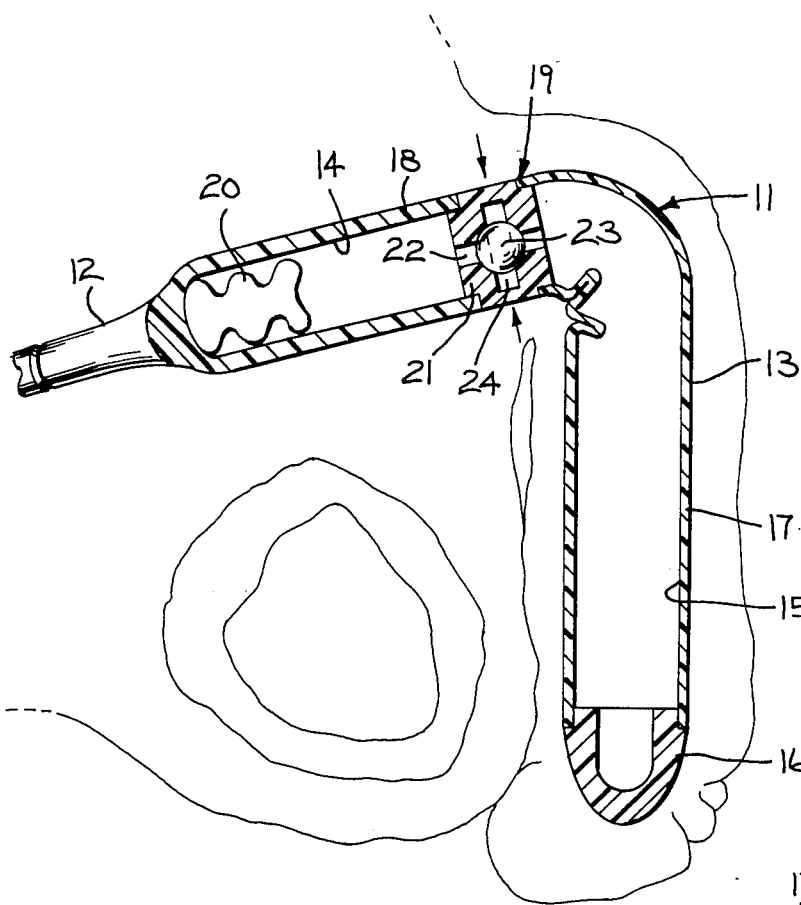
FIG. 1 is a side view, partly in section, of a preferred embodiment of the penile implant of the present invention with a gas filled bladder in the reservoir. One of the two identical penile implants is shown surgically implanted in a male and in a non-pressurized condition.

The preferred penile erectile system, which is shown in FIGS. 1-4, comprises a pair of cylindrical penile implants which are to be implanted in the corpora cavernosa of the penis. The two implants are identical, therefore, only one will be described in detail.

As seen in FIGS. 1 to 4 of the drawings, the implant 11 is a generally cylindrical member with a short proximal stem 12 and a longer distal portion 13 including a fluid reservoir 14, a pressure chamber 15 and a conical distal tip 16. The stem 12 which is of a relatively stiff material is implanted in the root end of a corpus cavernosum. The reservoir 14 of the distal portion 13 is implanted in the corpus near the base adjacent the stem 12 and the pressure chamber 15 and the tip 16 are implanted in the portion of the corpus in the pendulous penis. Each of the two implants is postioned in a separate corpus cavernosum of the penis.

The pressure chamber 15 of the implant 11 has a wall 17 of a flexible, non-distensible material so that the chamber 15 does not expand significantly in volume when pressurized but instead becomes stiff and rigid. The wall 17 is preferably of a material such as reinforced silicone rubber or polyurethane which either does not stretch or stretches only a given amount. The wall 18 of the reservoir 14 also is non-distensible, and it is preferably thicker to contain the fluid pressure and stiffer and less flexible than the wall 17. The necessary fluid tight seals between the walls 17, 18, the stem 12 and tip 16 may be made with a silicone adhesive or by other suitable means.

When the implant 11 is in a nonpressurized state as seen in FIG. 1, the chamber 15 is substantially filled with a non-compressible hydraulic fluid (not seen) which is biocompatible, such as saline or a free flowing silicone gel. In the non-pressurized state, the distal portion 13, including chamber 15, flexes and permits the penis to assume a substantially normal, flaccid position.

Figure 2:
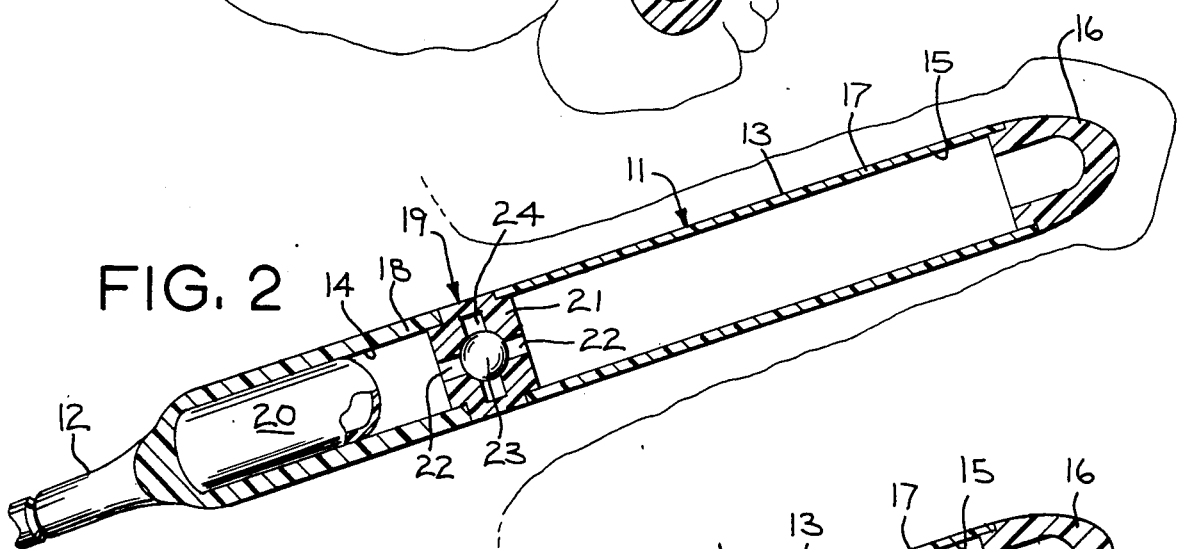
FIG. 2 is a side view similar to FIG. 1, except that the implant is pressurized.

Turning to FIG. 2, it can be seen that when the chamber 15 of implant 11 is pressurized, the distal portion 13 is rigid as the result of the chamber 15 being completely filled with fluid under pressure. The penis then assumes an erectile position.

The means for transferring fluid from the reservoir 14 to the chamber 15 and the valve means 19 for controlling fluid flow will now be described in connection with FIGS. 1 to 4.

As seen in FIGS. 1 to 4, the means for transferring fluid to the pressure chamber 15 is a gas filled bladder 20 positioned in the reservoir 14. The bladder 20 is preferably filled with $CO_2$ gas at about 1000 to 2000 cm $H_2O$ and preferably more than 1500 cm $H_2O$.

In FIG. 1, the bladder 20 and its gas contents are compressed and partially collapsed because the fluid pressure in the reservoir 14.

In FIG. 2, the bladder 20 is fully expanded and no longer collapsed because the fluid pressure in the reservoir 14 is now less than the gas pressure in the bladder 20. The pressurizing fluid in the reservoir 14 in the non-pressurized state has been transferred to the pressure chamber 15 by opening the valve means 19 and permitting the bladder 20 to expand and force the fluid into the pressure chamber 15.

The valve means 19 controls the fluid flow between the reservoir 14 and the pressure chamber 15. The valve means 19 includes a deformable valve body 21 which has a passage 22 which leads from the reservoir 14 to the pressure chamber 15. A ball 23 is located in an enlarged portion 24 of the passage 22 normally preventing the flow of fluid through the passage 22 between reservoir 14 and chamber 15. The valve means 19 is normally closed, but it can be opened by manipulation from the outside by deforming the valve body 21 to create leak paths 25 in the passage 22 about the ball 23 (seen best in FIG. 4). When the passage 22 is opened by squeezing and deforming the valve body 21 to create the leak paths 25, the pressure on the bladder 20 in reservoir 14 is relieved and fluid is forced out of the reservoir 14 into the pressure chamber 15 by the expansion of the bladder 20. The pressure of the gas in the bladder 20 causes it to expand to its full size which results in sufficient fluid being transferred to completely fill the pressure chamber 15 and make it rigid.

Figure 3:
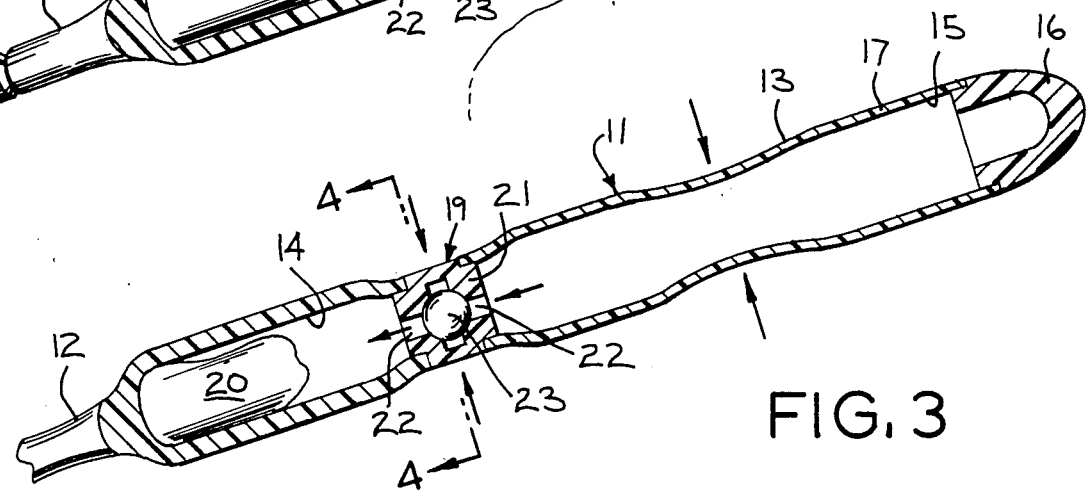
FIG. 3 is a side view similar to FIG. 2, showing the pressure chamber being depressurized.

As seen in FIG. 3, when it is desired to cause the implant 11 to assume the normal non-erectile position seen in FIG. 1, the pressure chamber 15 is depressurized by either simultaneously bending or squeezing the distal portion 13 and deforming the valve body 21 to create leak paths 25 about the ball 23 thus permitting fluid to return to the reservoir 14. The squeezing of the pressure chamber 15 causes the fluid pressure in the pressure chamber to rise and the pressurizing fluid to flow under pressure from the pressure chamber 15 back into the reservoir 14. The resulting increased fluid pressure in the reservoir 14 causes the gas filled bladder 20 to once again to contract or collapse. When sufficient fluid is transferred to the reservoir 14, and the distal portion 13 feels soft, the deforming force on the valve body 21 and the bending or squeezing of the distal portion 13 are stopped whereupon the implant 11 again assumes the flaccid state seen in FIG. 1.

In the embodiment of FIGS. 1 to 4 the wall 18 of the reservoir 14 must be strong enough to withstand the fluid pressures required to function and the wall 17 of the pressure chamber 15 must be sufficiently non-distensible to provide rigidity sufficient to support an erection when the chamber 15 is pressurized. The exact dimensions and materials of the walls are not critical so long as the walls possess the properties required to provide their desired functions.

In FIG. 5 an alternative valve system is shown that consists of a ball valve similar to that of FIGS. 1 and 4 and a pressure regulating valve similar to that of my earlier U.S. Pat. No. 4,364,379, which is incorporated by reference herein. The pressure regulating valve is set to open at pressures higher than those generated in the pressure chamber during intercourse. With such a valve system the pressure chamber is pressurized by manipulating the ball valve open and is depressurized by bending the pressure chamber to generate a high enough pressure to open the pressure regulating valve. The valve system makes it unnecessary to manipulate the valve to affect depressurization; bending the pressure chamber is sufficient to generate valve opening pressures.

In FIGS. 6 to 8, another embodiment of the implant of the present invention is seen.

In the implant of FIGS. 6 to 8, the stem 12, distal portion 13, and tip 16 are similar to those of the embodiment of FIGS. 1 to 4. However, the fluid transferring means is a spring driven piston 26. The piston 26 is normally retained in the compressed state seen in FIG. 6 by the fluid pressure in the reservoir 14 which is sensed by the face 27 of the piston 26. However, when the fluid pressure in reservoir 14 is relieved or falls below the force required to compress the spring 28 the fluid in reservoir 14, which is in front of the piston face 27, is forceably driven under pressure into the pressure chamber 15 by the movement of the piston as a result of the expansion of the spring 28.

In FIG. 6 the implant is shown in its normal flaccid state and in FIG. 7 it is shown pressurized and rigid.

In FIG. 8 the implant is shown being depressurized by forces being simultaneously exerted on the pressure chamber 15 to reduce its volume and on the valve 28 to deform and open it to fluid flow. As the fluid flows back into the area of the reservoir 14 adjacent the stem 12 the walls of that area resume the non-depressed state seen in FIG. 6.

The valve 29 shown in the embodiments of FIGS. 6 to 8 has a deformable valve body 30 with a passage 31 closed at each end by deformable membranes 32, 33. However, if desired, the ball valve of the embodiment of FIGS. 1 to 4 can also be used. The only requirements of the valve are that it is normally closed and that it can be opened from the outside by manipulation.

Figure 9:
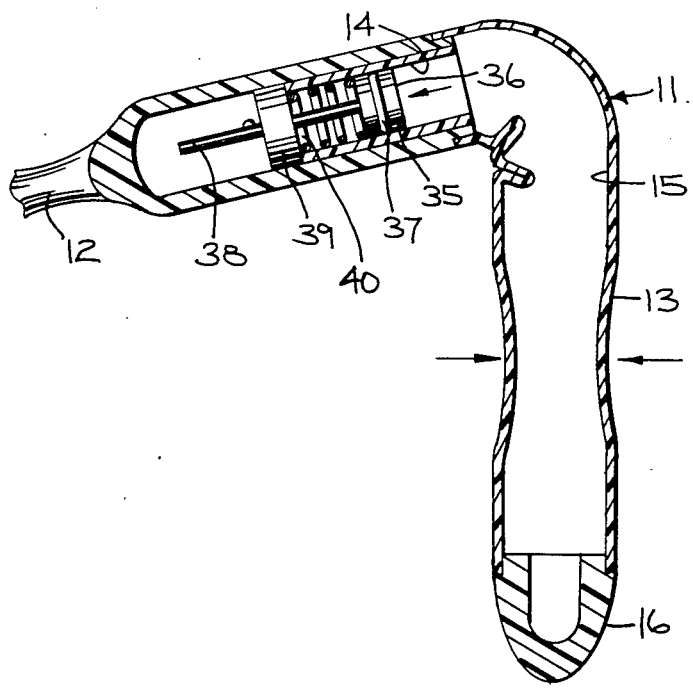
FIG. 9 is a side view, partly in section, of another penile implant of the present invention with a spring driven piston.
Figure 10:
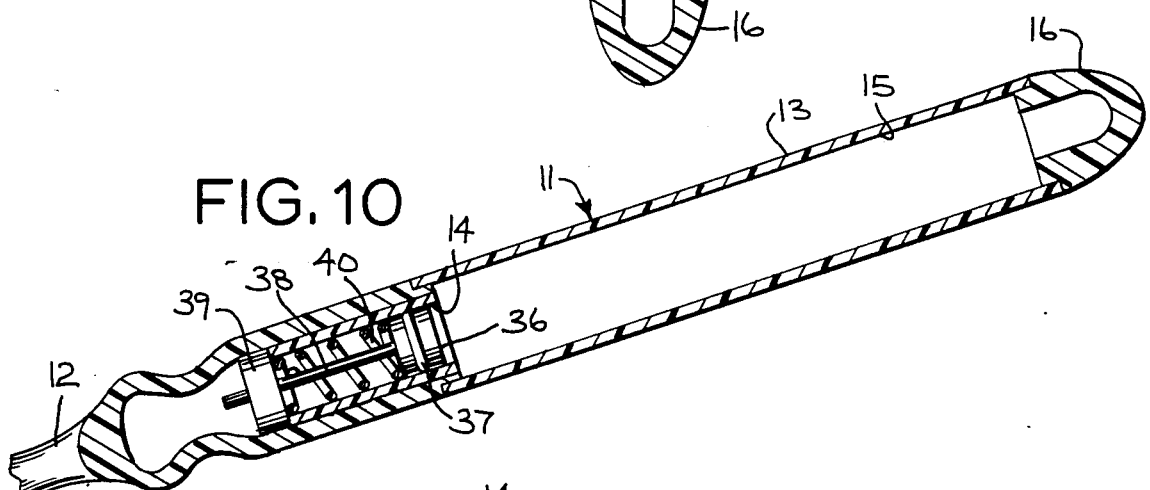
FIG. 10 is a side view similar to FIG. 8 with the implant pressurized.
Figure 11:
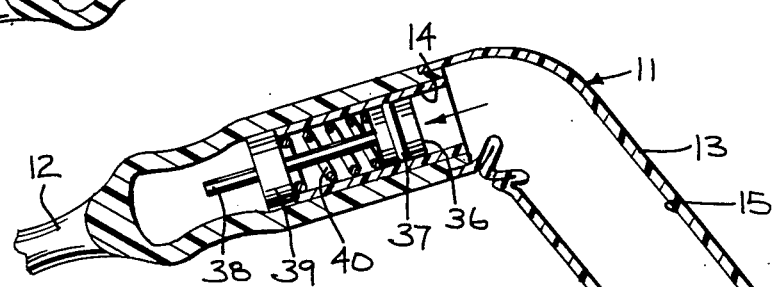
FIG. 11 is a side view similar to FIG. 8 showing the pressure chamber being depressurized.

In FIGS. 9 to 11, another embodiment of an implant having a spring driven piston is shown. The embodiment is similar to that of FIGS. 6 to 8, but there is no valve means.

As seen in FIG. 9, the implant 11 has a piston 34 having a piston head 35 mounted within the reservoir 14. The piston head 35 has a front piston face 36 and a resilient piston ring 37 forms a fluid tight seal with the wall of the reservoir 14. The fluid tight seal provided by the piston ring 37 permits the areas on opposite sides of the piston head 35 to be maintained at separate and different fluid pressures. A piston rod 38 extends from the back of the piston head 35 to a ball point pen type latch and unlatch mechanism generally referred to as 39.

The latch and unlatch mechanism 39 can be a relatively simple one such as those used in ball point pens and the like. Suitable mechanisms are described in U.S. Pat. Nos. 3,237,604 and 3,810,201 which are incorporated by reference herein.

The implant of FIGS. 9 to 11 may be pressurized by exerting pressure on the piston face 37 by bending or squeezing the pressure cylinder 15 as seen in FIG. 9. When the internal fluid pressure in chamber 15 drives the piston 34 back from its resting position the latch mechanism is disengaged and the piston 34 is driven forward by the spring 40 transferring the fluid in the reservoir before the piston face 36 into the pressure chamber 15 causing it to become rigid as seen in FIG. 10. The pressure chamber 15 can be depressurized by either squeezing or bending the pressure chamber 15 as seen in FIG. 11, to raise the fluid pressure in chamber 15 and to thus overcome the force of the spring 40 to force the piston 34 back into the latched position.

All the components of the described implants are preferably made of biocompatible materials having the necessary properties to function as intended.

The term "substantially filled" as used herein to describe the fluid content of a chamber in the penile implant means that a chamber contains about 60% to about 95% or more of its capacity of a non-compressible fluid such as water, saline or a free flowing gel. The actual content of fluid can vary; however, the implant when "substantially filled" should be still sufficiently flexible so that the penis can assume a normal flaccid position.

The term "non-distensible" as used herein is intended to cover materials or components which do not distend or distend to only a limited extent which still permits the device to function as intended.

All the parts and components of the prosthesis, except for the springs which may be of stainless steel, are preferably made of or covered with medical grade silicone rubber which is non-reactive, non-toxic and well tolerated by the adjacent organic tissues. Silicone rubber is preferred because it is quite resistant to wear and remains functional for long period of time. However, other suitable materials possessing desirable properties may also be employed.

The preferred method of implantation of the erectile systems of FIGS. 1 to 11 is through an incision made in the penis. After appropriate incision, each corpus cavernosum is dilated distally and proximally to accept the implants. The appropriate anatomical measurements are made to insure that the proximal end of the implant or implants will be positioned is the proximal crus. An appropriately sized implant is then inserted into the corpus cavernosum of the penis. The distal tip is positioned in the glans end of the corpus cavernosum. The stem at the proximal end of the implant is anchored in the root end of the corpus cavernosum.

The identical procedure is performed on the other side of the penis to complete the surgical procedure. The stems of the two implants preferably will diverge laterally to accommodate the anatomy, to provide lateral stability to the penis and to help prevent rotation of the implants. The incision is then closed.

It will be understood that the foregoing description has been for purposes of illustration, and a number of changes may be made without departing from the spirit and scope of the invention. Therefore, the invention is not to be limited except by the claims which follow.

I claim:

1. A valveless self-contained penile implant consisting essentially of an elongated, hollow, non-distensible cylinder having a flexible collapsible portion at one end for implanting into a corpus cavernosum of a pendulous penis and a relatively rigid other end for implanting in the root end of said corpus, pressurizing fluid substantially filling said hollow cylinder; a spring actuated, extendable piston closely fit in a longitudinal bore at the other end of said cylinder, said piston being extendable to transfer pressurizing fluid from the bore into said flexible, collapsible portion to thereby fill it and make it rigid; and, means for maintaining the spring actuated piston in a non-extended state until it is desired to tranfer the fluid into the flexible collapsible portion.

2. A valveless implant of claim 1 in which the means for maintaining the spring actuated piston in a non-extended state is a latch/unlatch mechanism.

* * * * *